(12) United States Patent
Shubat et al.

(10) Patent No.: US 10,317,381 B2
(45) Date of Patent: Jun. 11, 2019

(54) METHOD FOR MEASURING HYDROGEN PEROXIDE IN WATER

(71) Applicant: SPI TECHNOLOGY LTD., Ottawa, ON (CA)

(72) Inventors: Jim Shubat, Ottawa (CA); Gerben Op Den Buijs, Veldhoven (NL); Ludo Feyen, Heusden-Zolder (BE)

(*) Notice: Subject to any disclaimer, the term of this patent is extended or adjusted under 35 U.S.C. 154(b) by 29 days.

(21) Appl. No.: 15/799,332

(22) Filed: Oct. 31, 2017

(65) Prior Publication Data

US 2018/0059077 A1   Mar. 1, 2018

Related U.S. Application Data

(62) Division of application No. 14/292,593, filed on May 30, 2014, now Pat. No. 9,835,601.

(60) Provisional application No. 62/001,204, filed on May 21, 2014.

(51) Int. Cl.
| | |
|---|---|
| G01N 33/00 | (2006.01) |
| G01N 31/22 | (2006.01) |
| G01N 21/78 | (2006.01) |
| G01N 21/27 | (2006.01) |
| G01N 21/31 | (2006.01) |
| G01N 21/33 | (2006.01) |
| G01N 33/18 | (2006.01) |

(52) U.S. Cl.
CPC ......... *G01N 31/228* (2013.01); *G01N 21/272* (2013.01); *G01N 21/31* (2013.01); *G01N 21/33* (2013.01); *G01N 21/78* (2013.01); *G01N 33/18* (2013.01); *G01N 2201/062* (2013.01)

(58) Field of Classification Search
CPC ...................................... G01N 33/00
USPC ...... 436/43, 135, 164, 172; 422/68.1, 82.05, 422/82.09
See application file for complete search history.

(56) References Cited

U.S. PATENT DOCUMENTS

| | | | | |
|---|---|---|---|---|
| 4,143,080 | A | * | 3/1979 | Harders .................. C12Q 1/28 436/66 |
| 4,587,100 | A | * | 5/1986 | Amano .................. C12Q 1/28 422/423 |
| 5,474,938 | A | | 12/1995 | Jadesjo et al. |
| 5,582,741 | A | | 12/1996 | Kenmoku et al. |
| 6,269,680 | B1 | | 8/2001 | Prieve et al. |
| 6,653,095 | B1 | | 11/2003 | Gwy et al. |
| 2002/0185448 | A1 | | 12/2002 | Chisholm et al. |
| 2003/0025909 | A1 | | 2/2003 | Hallstadius |
| 2004/0048329 | A1 | | 3/2004 | Beuermann |
| 2008/0305553 | A1 | | 12/2008 | Kraus |
| 2011/0070654 | A1 | | 3/2011 | Tokhtuev et al. |
| 2012/0028364 | A1 | * | 2/2012 | Kraus ................ G01N 35/1095 436/127 |
| 2017/0305768 | A1 | * | 10/2017 | Shubat .................... C02F 1/722 |

* cited by examiner

*Primary Examiner* — Brian J. Sines

(57) ABSTRACT

An apparatus and method for measuring hydrogen peroxide concentration in water to an accuracy of 0.1 ppm comprises a colorimetric assay method to determine hydrogen peroxide concentration. The assay is monitored spectophotometrically at a desired wavelength. Each sample is corrected relative to a control sample and hydrogen peroxide concentration determined with respect to a standard curve.

9 Claims, 7 Drawing Sheets

METHOD FOR MEASURING HYDROGEN PEROXIDE IN WATER

CROSS REFERENCE TO RELATED APPLICATIONS

This application is a divisional of U.S. patent application Ser. No. 14/292,593, filed on May 30, 2014, allowed on Aug. 14, 2017, and claims the benefit of U.S. Provisional Patent Application 62/001,204, filed on May 21, 2014, both of which are incorporated by reference in their entirety.

FIELD OF INVENTION

The present invention relates to an apparatus and method for measuring hydrogen peroxide to an accuracy of 0.1 ppm in water, particularly in drinking water.

BACKGROUND

Stabilized hydrogen peroxide solutions used for water disinfection, such as HUWA-SAN™ owned by Roam Chemie NV of Houthalen, Belgium, and SANOSIL™ owned by Sanosil Ltd. of Hombrechtikon, Switzerland are known in the art. Such hydrogen peroxide ($H_2O_2$) solutions are proprietary and are stabilized by silver ions or silver colloid in minute concentrations. Other stabilized hydrogen peroxide solutions are stabilized by alcohols, acids or other compounds. Depending on the solution, the stabilizer prevents the hydrogen peroxide from oxidizing too quickly when it contacts water, thereby allowing the solution to mix with the water before binding to and disinfecting undesirable microorganisms and chemicals.

Various apparatuses exist to measure the concentration of hydrogen peroxide in water including with chemiluminescent, fluorometric, amperometric and colorimetric sensors. The prior art sensors and detection systems were built to measure hydrogen peroxide concentration thresholds in swimming pool water treatment systems where regulations allow maximum levels not to exceed, for example, 150 mg/L (150 ppm), and typical operating concentrations are between 50-100 ppm. Other regulations have standards in the same order of magnitude.

In drinking water regulation, however, the acceptable concentration thresholds are much lower, often in the order of under 10 ppm. For example, in Ontario, Canada, operating concentrations for drinking water are between 2-8 ppm. Existing detection methods are inadequate to quickly measure the concentration of hydrogen peroxide in water at such low levels at an accuracy better than ±3 ppm.

There is a need for a measurement apparatus and method to quickly detect low concentrations of hydrogen peroxide in water, including drinking water, in the order of 10.0 ppm or less and to an accuracy of 0.1 ppm. Such techniques must not be affected by pH, temperature or water composition.

SUMMARY OF THE INVENTION

In a first aspect of the invention, an apparatus for measuring hydrogen peroxide levels in water using a colorimetric assay method is provided. The apparatus comprises a measurement cell for containing a water sample; a light transmitter configured to emit light at a selected wavelength at the measurement cell; a photodiode receiver configured to receive light passing through the measurement cell and a reagent in a reagent vial. The reagent comprises a reagent compound configured to react with hydrogen peroxide to form a reaction product, the reaction product is adapted to absorb light at the selected wavelength proportional to the amount of hydrogen peroxide in the water sample. The apparatus also comprises a surfactant and a solvent. Within the apparatus, there is a first network of pipes connecting source water to a buffer jar, the buffer jar to a supply valve, the supply valve to the apparatus measurement cell, and a second network of pipes connecting the reagent vial to a reagent valve, the reagent valve to the measurement cell, and the measurement cell to a drain valve; and a control unit; the control unit is configured to cause a first colorimetric measurement of a first water sample free of reagent and a second colorimetric measurement of a second water sample mixed with reagent. The control unit determines the difference between the first and second measurements and compares the difference against a pre-determined standard curve of diluted hydrogen peroxide to determine and report the concentration of hydrogen peroxide in the water sample, accurate to 0.1 mg/L.

In one embodiment the reagent compound is potassium bis (oxalato) oxotitanate (IV) DI.

In another embodiment, the selected wavelength is 470 nm.

In a further embodiment the light transmitter is a LED light emitter.

In another embodiment the reagent comprises potassium bis (oxalato) oxotitanate (IV) DI, EDTA di-sodium salt dihydrate and polyoxyethylene (23) lauryl ether mixed in a solvent.

In one embodiment the solvent is sulfuric acid 99%: p.a. 10% solution.

In a further embodiment the predetermined standard curve comprises data points from 0 ppm to 150 ppm.

In another embodiment the predetermined standard curve comprises data points from 0 ppm to 100 ppm.

In another aspect of the invention, there is provided a method of measuring hydrogen peroxide levels in water using a colorimetric assay comprising transferring a first water sample to a measuring cell; determining a first absorbance measurement of light at a selected wavelength as a null measurement; removing the first sample from the measurement cell; transferring an aliquot of a reagent consisting of a reagent compound configured to react with hydrogen peroxide to form a reaction product, the reaction product adapted to absorb light at the selected wavelength proportional to the amount of hydrogen peroxide in the water sample to the measurement cell; filling the measurement cell with a second water sample; determining a second absorbance measurement of light at the selected wavelength as a test measurement; emptying the measurement cell and rinsing with sample water; and a control unit adapted to determine the difference between the first and second measurements and compare the difference against a pre-determined standard curve of diluted hydrogen peroxide to determine and report the concentration of hydrogen peroxide in the water sample to an accuracy of 0.1 mg/L.

In another embodiment the method uses the reagent compound potassium bis (oxalato) oxotitanate (IV) DI.

A further embodiment of the method relates to the selected wavelength is 470 nm.

Another embodiment of the invention provides the reagent comprising potassium bis (oxalato) oxotitanate (IV) DI, EDTA di-sodium salt dihydrate and polyoxyethylene (23) lauryl ether mixed in a solvent.

In another embodiment the solvent is sulfuric acid 99%: p.a. 10% solution.

In one embodiment the predetermined standard curve comprises data points from 0 ppm to 150 ppm.

In a further embodiment the predetermined standard curve comprises data points from 0 ppm to 100 ppm.

BRIEF DESCRIPTION OF THE DRAWINGS

Embodiments are illustrated by way of example and not limitation in the following figures, in which like references indicate similar elements.

DETAILED DESCRIPTION

Example embodiments, as described below, may be used to provide an apparatus and method to quickly measure hydrogen peroxide in water at very low concentrations.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In the case of conflict, the present specification, including definitions, will control. In addition, the materials, methods, and examples are illustrative only and not intended to be limiting.

The present invention is a colorimetric assay method to determine hydrogen peroxide concentration. A colorimetric method is based on production of a reaction product that absorbs light at a selected wavelength. Preferably a reagent compound used to produce the reaction product does not have significant light absorption properties at the selected wavelength. Formation of the reaction product is proportional to the amount of hydrogen peroxide in the water sample. Quantification of the reaction product is measured and converted to a $H_2O_2$ concentration based on a standard curve.

A preferred colorimetric method is based on production of a reaction product that produces a yellow to orange coloured complex when potassium bis(oxalato)-oxotitanate (IV) reacts with hydrogen peroxide to form a reaction product adapted to absorb light at 470 nm proportional to the amount of hydrogen peroxide in the sample. Quantification of the reaction product is measured at 470 nm and converted to a $H_2O_2$ concentration based on a calibration curve. The photodiode measurement data produced by the reaction product of the above reactant with $H_2O_2$ has been determined to correlate logarithmically with $H_2O_2$ concentration. Alternatively, other wavelengths may be used such as 400 nm. The wavelength that gives the maximum absorbance of a coloured reaction product is one consideration in choosing a selected wavelength. Additionally the resulting standard curve and degree of linearity that can be achieved may vary at each wavelength. In one embodiment of the present invention, the wavelength is selected to be 470 nm. The standard curve generated with this data produces a close to linear standard curve and a high degree of accuracy is thereby achieved. Other wavelengths of light are contemplated.

One objective is to obtain the greatest accuracy by facilitating the closest possible adherence to the Lambert Beer principles of light absorption between the transmitter and receiver, in accordance with the formula:

$$\frac{I_1}{I_0} = 10^{-E} = 10^{-eed}$$

Figure 1:
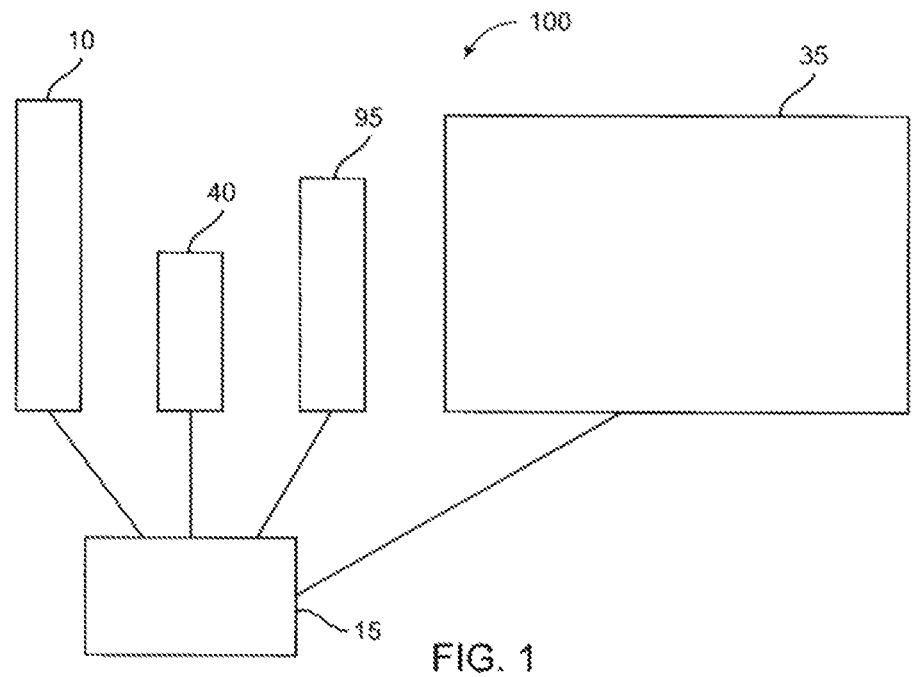
FIG. 1 is a box diagram of one embodiment of an apparatus of the present invention.

In one embodiment, an apparatus 100 is provided in FIG. 1. The main components of the apparatus 100 include control unit 35, measurement cell 15, buffer jar 10, reagent vial 40 and, to a lesser extent, riser tube 95.

Water flowing in a system, such as a water treatment and distribution system, comprises an unknown quantity of dosed stabilized hydrogen peroxide, which acts as a disinfectant. In one embodiment the dosed stabilized hydrogen peroxide is HUWA-SAN 25. The use of other stabilized hydrogen peroxides is contemplated at various concentrations.

Figure 2:
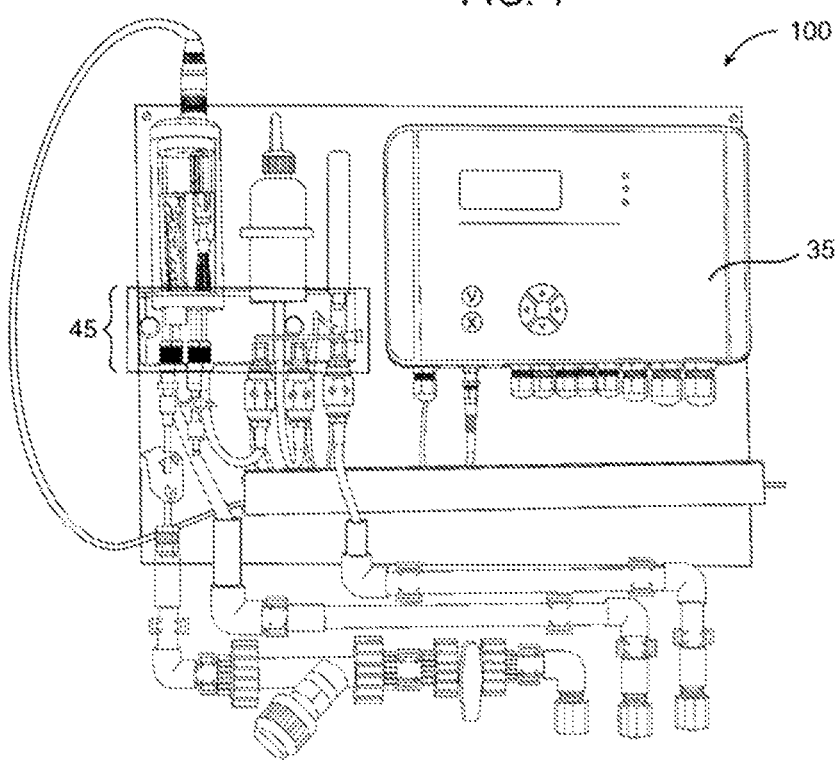
FIG. 2 is a diagram of one embodiment of FIG. 1 showing the analysis unit and control unit.

As shown in FIG. 2, there is provided apparatus 100 in accordance with one embodiment of the present invention. A close-up diagram of apparatus 100 is provided in FIG. 3, which includes a further close-up diagram of buffer jar 10. Apparatus 100 diverts water from the system and into buffer jar 10. Buffer jar 10 serves as a reservoir from where a water sample can be directed to a measuring cell 15 at a desired time interval. An overflow tube 50 returns water to the system, thereby maintaining a constant volume in the buffer jar 10 and a turn-over of water in the buffer jar 10. Water exiting buffer jar 10 may first pass through a filter 55 to remove particulate matter. Optionally a filter may be installed prior to water entering buffer jar 10 or in such other locations as to prevent or limit particulate matter from entering apparatus 100. Sample water flow is directed from the buffer jar 10 to the measurement cell under control of a supply valve 60, reagent is directed to the measurement cell under control of a reagent valve 70, and a drain valve 80 operates to control fluid retention in, or draining of, the measurement cell 15. Outflow from the measurement cell 15 is directed to a waste drain 90. The measurement cell 15 has an upper opening and a lower opening 105. The lower opening is connected to a network of piping to allow filling and emptying of the measurement cell 15 with sample water and reagent as required. The upper opening is connected to a riser tube 95. The riser tube 95 extends upward to at least the height of the water level in the buffer jar 10. The riser tube 95 increases the efficiency of rinsing the measurement cell 15 by providing added volume and force of the water movement. Plumbing connects the elements to provide a conduit for fluid flow. For example, a first network of pipes connecting the source water to the buffer jar 10, the buffer jar 10 to the supply valve 60, the supply valve 60 to the measurement cell 15, and a second network of pipes connecting the reagent vial 40 to the reagent valve 70, the reagent valve 70 to the measurement cell 15, the measurement cell 15 to the drain valve 80, and the drain valve 80 to the waste drain 90. Such plumbing can be composed of PVC piping, or flexible tubing such as Tygon™ tubing, a combination thereof, or other such conduit as desired.

Figure 5:
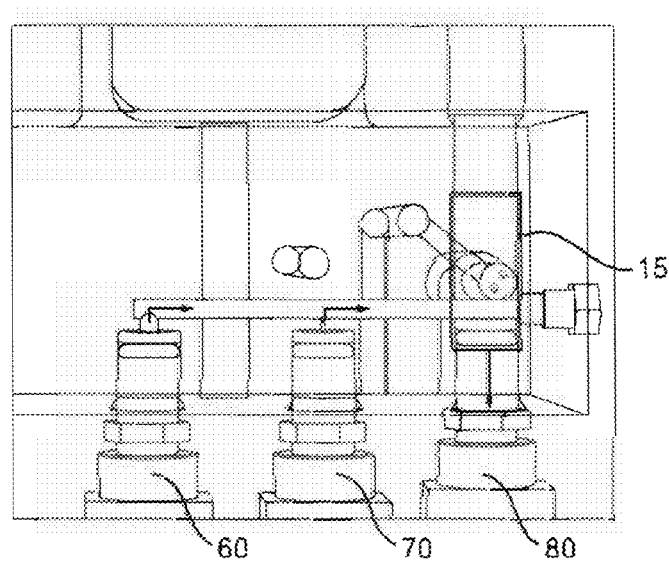
FIG. 5 is a schematic of a close-up of the apparatus of FIG. 2 showing the direction of flow and measurement cell.

The direction of flow of the various fluids is depicted in FIG. 5, showing (by arrows) the supply sample fluid flow through supply valve 60, the supply reagent fluid flow from reagent valve 70 and the cell drainage from measurement cell 15 through drain valve 80.

In one embodiment, an apparatus 100 is provided that receives water from a system into a buffer jar 10, draws a first water sample from the buffer jar into a measurement cell 15 to determine a null or background reference measurement, removes the first sample, draws an aliquot of reagent from a reagent vial 40 into the measurement cell 15 and draws a second water sample from the buffer jar 10 into the measurement cell 15 to determine a sample measurement. The null measurement is subtracted from the sample measurement and the difference value is interpreted relative to a standard curve for a determination of hydrogen peroxide concentration. A standard curve can be represented graphically or by mathematical expression of the curve. The mathematical expression is useful in a digital system.

Figure 3:
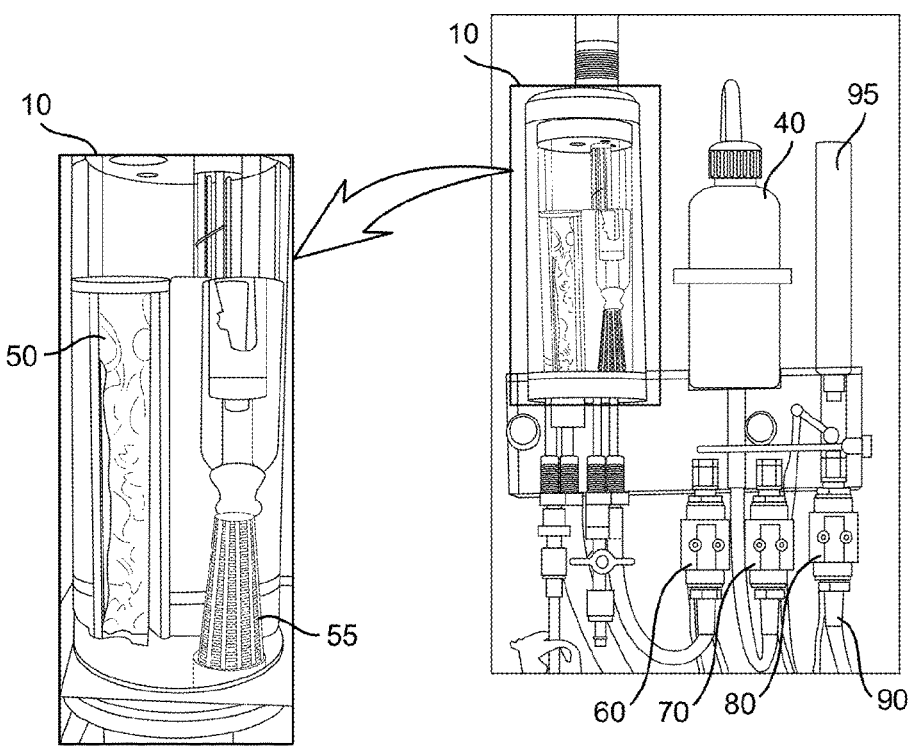
FIG. 3 is a close-up diagram of FIG. 2 including an expanded portion illustrating the buffer jar.
Figure 4:
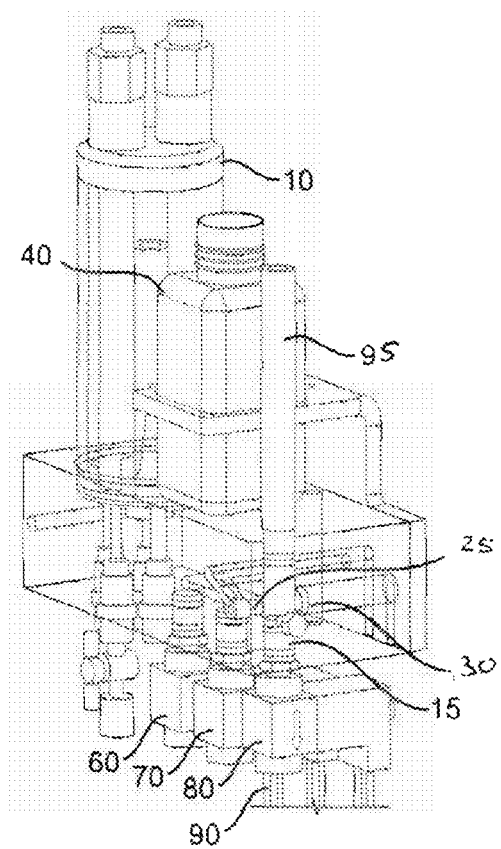
FIG. 4 is a schematic of a close-up of the apparatus of FIG. 2 showing the buffer jar, reagent vial and measurement cell.

A side perspective view of FIG. 3 is provided in FIG. 4, showing light emitter 25 and light receiver 30 on either side of measurement cell 15. The size and design of the measurement cell 15 will influence the accuracy and efficiency of the measurement. Factors may include, but are not limited to, the path length from a light emitter 25 to a light receiver 30, the light yield of the light source and the sensitivity of the light receiver 30, the measurement cell 15 composition and cell wall thickness, and distance between emitter 25 and receiver 30 elements. The physical parameters such as measurement cell wall thickness, path length and photodiode emitter and receiver equipment are fixed once chosen and therefore can be compensated by hardware calibration and system settings. In a preferred embodiment, measurement cell 15 was custom milled from a single piece of thermoplastic polycarbonate, such as Lexan™, with known techniques such as a CNC mill station.

In one embodiment, the measurement cell 15 has a width of 10 mm; cell wall thickness of 1 mm, and cell height is 19.5 mm. A measurement cell of these dimensions produces a sample volume of about 2 mL. Other volumes are contemplated. These parameters were selected as optimal dimensions for this embodiment given a number of factors including sufficient sample size for greatest accuracy and precision, as well as cost. The material used for the measurement cell was chosen based on light transmission capabilities and resistance to degradation from water and chemical reagents. All channels were polished to a high transparency level to maximize light transmission. Measurement cell 15 was polished on the inside to enable maximum light transmission.

Figure 6:
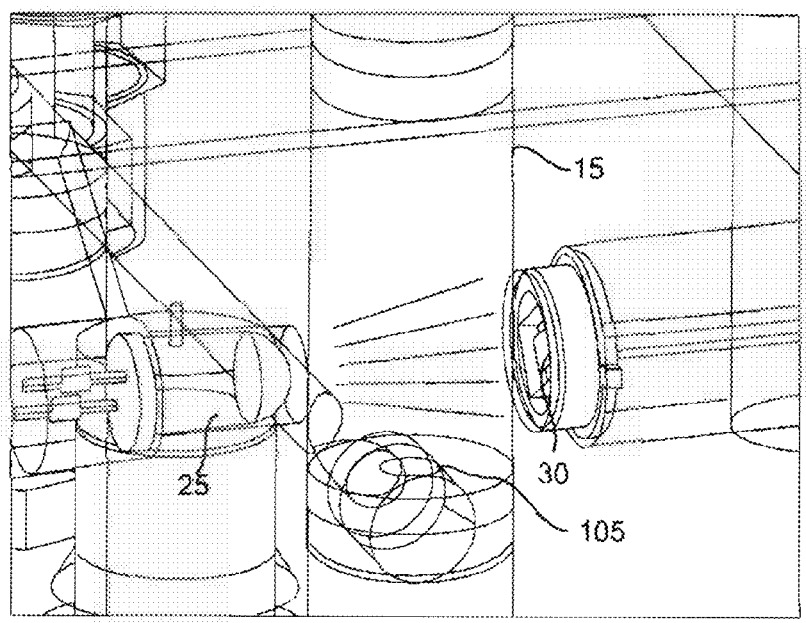
FIG. 6 is a schematic of a close-up of the apparatus of FIG. 1 showing the measuring cell, LED and receiver.

The measurement chamber shown in FIG. 6 comprises a light source 25 to emit light at a selected wavelength, measurement cell 15, and a photodiode receiver 30. Preferably the light emitter 25 is a LED light which emits light at 470 nm. The light is transmitted through the walls of the measurement cell 15 containing the sample and the resulting non-absorbed light is captured on photodiode 30. A small current is generated in the photodiode 30, which is measured by an operational amplifier on the apparatus 100 and converted by an analog/digital (AD) convertor to an internal value of 1000, which is the resolution of the measurement processor. This is the null value or zero reagent sample.

Figure 9:
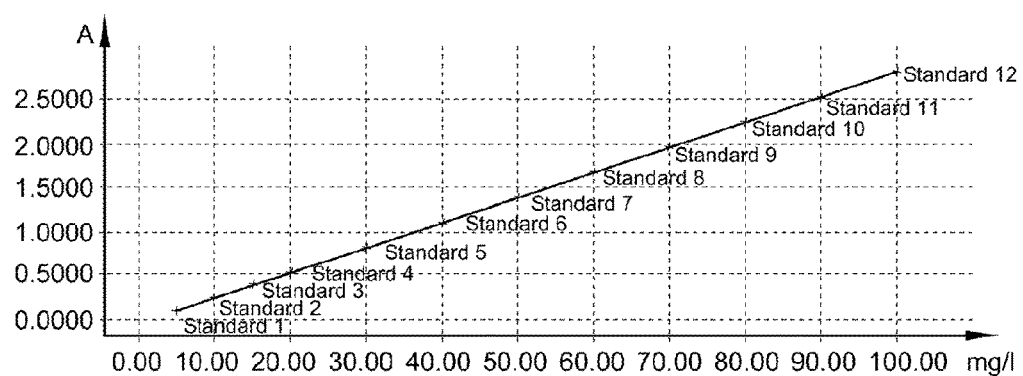
FIG. 9 is a pre-determined standard curve generated by plotting Absorbance data relative to concentration of hydrogen peroxide for use in determining the concentration of hydrogen peroxide in a measured test sample, in accordance with one embodiment of the present invention.

FIG. 9 shows a plot of absorption over concentration (mg/L) and establishes that the light absorption of the reaction product is linear in relation to the concentration of hydrogen peroxide. The raw data produced by the photodiode and that of the AD convertor results in a logarithmic relationship to $H_2O_2$ concentration. With respect to units used to express concentration of $H_2O_2$ both mg/L and ppm are commonly used. It is noted that 1 mg/L is equivalent to 1 ppm.

A reagent mixture was developed wherein a substrate reagent reacts with $H_2O_2$ to produce a reaction product in a stoichiometric relationship. The reaction product is detected spectrophotometrically at a selected wavelength and correlated to sample hydrogen peroxide concentration. Components of the reagent mixture do not interfere with the colorimetric measurement and are not effected by variable water characteristics such as water hardness or trace metal or organic components. An effective amount of a surfactant is optionally added to improve reagent mixture flow characteristics through the measurement cells and interconnecting channels.

In one embodiment, the reagent mixture comprises the following compounds: potassium bis (oxalato) oxotitanate (IV) DI (Merck KGaA, Darmstadt, Germany); EDTA disodium salt dihydrate Titriplex III™ (Merck KGaA, Darmstadt, Germany); Surfactant: Polyoxyethylene (23) lauryl ether Brij™ 35 (30%) (Sigma-Aldrich); disolved in a solvent of sulfuric acid 99%: p.a. 10% solution (Merck KGaA, Darmstadt, Germany).

The reagent mixture is prepared as follows for a 1,000 mL final volume, 50 g potassium bis (oxalato) oxotitanate (substrate reagent), 0.2 g EDTA di-sodium salt dehydrate, sulfuric acid 99% to a final dilution of 10%, and 1 ml of polyoxyethylene (23) lauryl ether.

Figure 7:
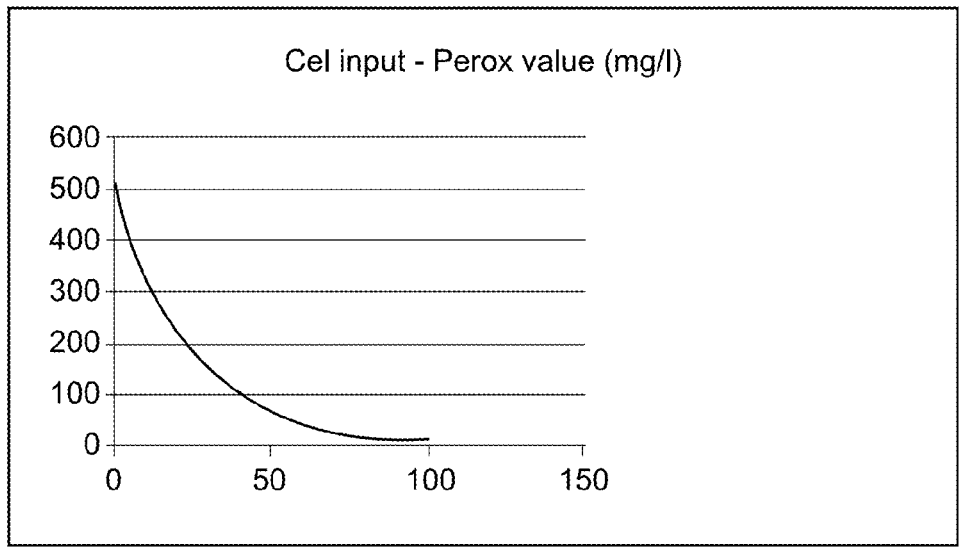
FIG. 7 is a chart of measured hydrogen peroxide concentration used to calibrate one embodiment of the apparatus of the present invention.

Prior to use, the apparatus 100 is calibrated. Samples having known concentrations of hydrogen peroxide are measured and a standard curve is created by plotting the observed measurement cell output signal measurement against the known concentration. This curve can be represented graphically (see FIG. 7) or by mathematical extrapolation. The concentration of hydrogen peroxide in an unknown sample is then determined with reference to the standard curve and the result reported, displayed or recorded either digitally, graphically or by other convenient means. Preferably, the standard curve includes a range of known samples spanning the range of concentrations to be measured, for example from 0-150 mg/L (ppm). The standard curve comprising data points in the desired range (i.e. 0-150 mg/L) greatly increases the accuracy of the determination and is key to providing an accuracy of 0.1 mg/L.

Figure 10:
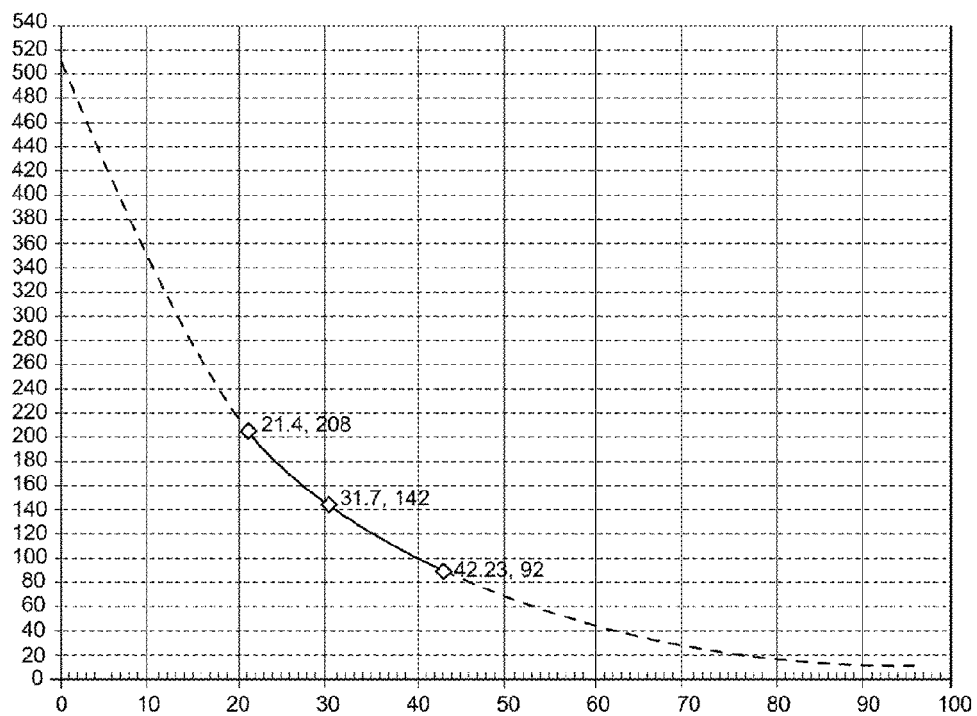
FIG. 10 is a pre-determined standard curve generated by plotting digitized measurement data relative to concentration of hydrogen peroxide for use in determining the concentration of hydrogen peroxide in a measured test sample in accordance with one embodiment of the present invention.

A known concentration of hydrogen peroxide is required in order to calibrate the apparatus. Perhydrol™ 30% for analysis EMSURE™ ACS, ISO from EMD Millipore Corporation of the Merck Group, was used. Other certified trade solutions can also be used so long as the accuracy is in the order of 99.999%. Standard solutions for spectrophotometric measurement are made between 0 to 100 mg/L which is the measurement range of the apparatus of the present invention. The concentrations of the Perhydrol dilutions are confirmed and validated through a standard titration method, for example iodometry. Subsequently a pre-determined number of measurements are carried out in the apparatus with these known concentrations and raw data (see Table 1) is generated to create a standard curve, as shown in FIG. 10.

TABLE 1

| mg/L | Raw Value | Raw Value With Correction (*511/480) |
|---|---|---|
| 0 | 480 | 511 |
| 5 | 384 | 409 |
| 10 | 309 | 329 |
| 15 | 245 | 261 |
| 20 | 201 | 214 |
| 30 | 134 | 143 |
| 40 | 93 | 99 |
| 50 | 60 | 64 |
| 60 | 42 | 45 |
| 70 | 31 | 33 |
| 80 | 24 | 26 |
| 90 | 20 | 21 |
| 100 | 12 | 13 |

The standard curve is used to calibrate apparatus 100. The value of raw value in Table 1 is the raw data of the measured sample at a scale of 0-480 as determined by the photodiode. A value of 480 represents 0% absorbance (100% transmission) and represents a zero or null sample reflecting that there is no hydrogen peroxide in the sample. The resolution of the Analogue-Digital (AD) convertor is 512 bit (0-511). Raw values are converted to digital values by multiplying by 511 and dividing by 480, a factor of 1.0646. The measured value is compensated for full scale. The standard curve is determined with the apparatus in one embodiment of the present invention, which measures in 10 bit resolution (1000 steps, 100 ppm/1,000=0.1 ppm resolution).

A standard curve is generated by using a number of data points. The standard curve becomes more accurate when more points are generated. Preferably, data points are biased in the lower range of detection, for example 0-20 ppm and cover the entire range of desired detection, for example 0-150 ppm. Once generated the standard curve can be represented mathematically for convenient use within an algorithm of the control unit 35. Example 2 describes a standard curve and the mathematical derivation of a $H_2O_2$ concentration based on the curve.

Calibration of the apparatus 100 to control for hardware variables is performed for each measurement cell. Hardware variables include wall thickness of measurement cell, specific path length between light emitter and photodiode light receiver, and the light yield of the light emitter and the sensitivity of the photodiode light receiver. Prior to use a calibration adjustment to compensate for hardware variables is performed. The measurement cell is filled with distilled water and the measurement signal that originates from the photodiode is then measured through an input potentiometer and adjusted to 1,000. This is the resolution of the measurement processor within the control unit 35. When replacing the measurement cell, adjustment to the photodiode or LED recalibration is essential.

Figure 8:
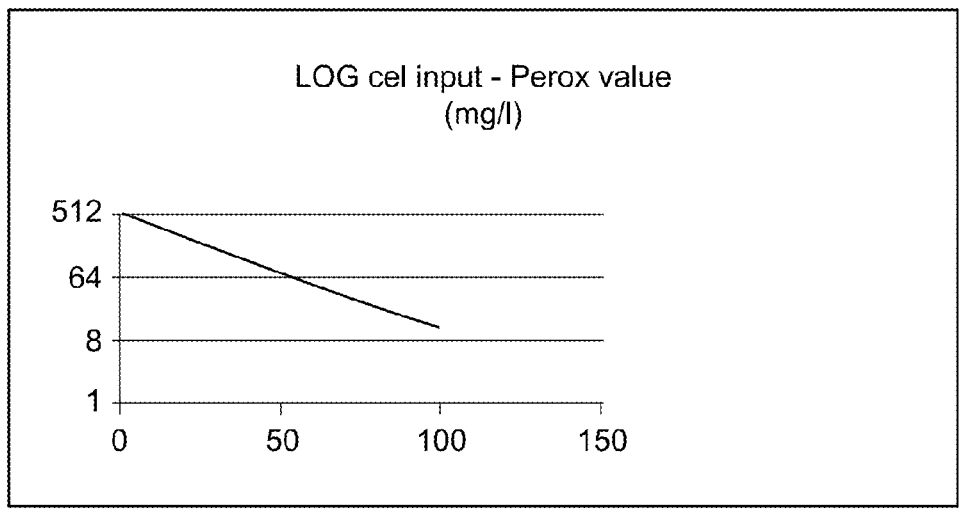
FIG. 8 is a logarithmic chart of hydrogen peroxide values generated to calibrate one embodiment of the apparatus of the present invention.

A pre-measurement software adjustment to the photodiode light receptor 30 sets the photodiode 30 to a value of 1,000 based on a control water sample present in the measurement cell 15. A test water sample containing added reagent produces the colored complex and absorbs more light in logarithmic dependence to the amount of hydrogen peroxide in the sample (see FIG. 8). Consequently, the light that is not absorbed reaches photodiode receiver 30, resulting in a relatively smaller current in comparison with the reagent-free sample measurement. A measurement of the test sample containing hydrogen peroxide will be lower than 1,000. The apparatus 100 measures the change in current. By adjusting for the measurement in the reagent-free sample, any absorbance due to water turbidity or composition of the water sample and chamber walls is accounted for.

To achieve maximum accuracy and sensitivity during operation the apparatus 100 will run a control sample (test water alone) as a reference point, a sample measurement is then made with sample water plus reagent. By factoring in the control sample at each test sample, variability in water composition and turbidity are controlled for and accuracy of the hydrogen peroxide concentration determination maximized. Preferably, an accuracy to 0.1 ppm is achieved.

In making a measurement, an aliquot of reagent is transferred from the reagent vial 40, and a water sample is transferred from buffer jar 10, into the measuring cell 15. The aliquot of reagent is kept small, however an excess of reagent compound can be provided such that in the measuring cell 15, hydrogen peroxide is the limiting reactant in the assay mixture. For a reagent mixture prepared as described above and a 1.5 mL sample volume, the volume of required reagent was 0.03 mL in one embodiment. This is suitable to provide accurate detection of hydrogen peroxide to a maximum water sample concentration of 100 ppm.

It is noted that the volumes of sample and reagent are measured precisely and consistently in order to achieve precise measurements. As such, a control system comprising a software algorithm is used to provide precise control of the valves in order to deliver the optimal amount of reagent to ensure accuracy. The valves are controlled by the control unit 35 in a time-dependent manner. A valve time refers to the length of time the valve is in the open position thereby allowing fluid flow. The valve time is correlated to a volume such that a known valve time will result in the movement of a known volume. These times may vary depending on the specific characteristics of the valve in use and are readily determined. In one embodiment, the reagent valve time has been set to 30 milliseconds to allow a reagent volume of 0.03 mL to pass the valve. Head pressure in the water or reagent system may affect the volume of fluid that passes the valve during a given valve time. Compensation may be made in a variety of means. For example, the buffer jar 10 maintains a constant volume and therefore maintains a constant head pressure, a similar reagent buffer jar may readily be incorporated into the system design. Alternatively, other designs may be incorporated to provide consistent pressures such as the use of a pressurized head space over the liquid. The control unit is programmed to provide the desired valve time at each step of the measurement cycle. For example valve times for flushing and rinsing of measurement cell are different than the valve time to add the volume for a test water sample. Other valve times are contemplated.

In one embodiment, the control unit 35 operates to measure hydrogen peroxide concentration in a water system by diverting samples to apparatus 100 on a periodic basis, such as every 2 minutes. Other time intervals are contemplated. The steps comprise:

Measurement cell 15 is filled with sample water;
Measurement cell 15 is emptied, flushing measurement cell 15 to keep it clean;
Measurement cell 15 is refilled with sample water;

Measurement is obtained and set as a zero measurement (null value);

Measurement cell 15 is emptied;

Measurement cell 15 receives an aliquot of reagent from reagent vial 40, and measurement cell 15 is filled with sample water;

Measurement is obtained as test measurement;

Empty measurement cell 15;

Fill and empty measurement cell 15 with sample water to rinse cell;

Fill and keep measurement cell 15 full until the next measurement is initiated.

The control unit includes analysis capability and determines the test sample hydrogen peroxide concentration by an algorithm that comprises the steps of: calculating the difference between null and test sample measurements; determining the concentration of hydrogen peroxide from a standard curve; reporting and/or recording the sample hydrogen peroxide concentration.

In a further embodiment, the valve time (the time the reagent valve is open) is variable and the control system calculates the required volume of reagent. The objective is to optimize reagent use. The control system calculates the average $H_2O_2$ concentration of at least the two previous samples and bases its next valve time on an expected $H_2O_2$ concentration. A limitation of this method results in inaccuracies when the hydrogen peroxide level fluctuates quickly, as the reagent dosing calculation lags the actual reagent requirement.

In an alternative embodiment, the control system is set to control valve time, and thus reagent volume, based on multiple measurements of each test sample. The results are used by the control system to adjust reagent volume as required. In one embodiment for a measurement of hydrogen peroxide in a test sample an aliquot of reagent is introduced into the measurement cell, the measurement cell is half filled with test sample and a measurement conducted and recorded, the measurement cell is then filled with test sample and a second measurement conducted. In one embodiment, Measurement 2 is approximately half the reading of Measurement 1. If Measurement 2 is much less than half of Measurement 1, reagent is the limiting reactant and more reagent is required in the following measurement sequence. If Measurement 2 is greater than half of Measurement 1, reagent is in excess and less reagent can be used in the following measurement sequence. If Measurement 2 is approximately half of Measurement 1, then the amount of reagent being used is optimal.

In an alternative embodiment, reagent use is optimized to conserve reagent while still ensuring that an excess of reagent is provided relative to the hydrogen peroxide concentration. At least two readings are obtained from one sample and used to determine reagent requirement. The control system sets the reagent dose for the subsequent test sample based on measurements obtained from a previous test sample. The steps are as follows:

Measurement cell 15 is filled with sample water;

Measurement cell 15 is emptied, flushing measurement cell 15 to keep it clean;

Measurement cell 15 is refilled with sample water;

Perform a zero measurement (null value);

Measurement cell 15 is emptied;

Measurement cell 15 is refilled but at the beginning of the fill cycle, a timed addition of reagent from vial 40 is added to the sample;

The measurement cell is filled halfway;

Measurement 1 is conducted;

The measurement cell is filled fully with sample water without the addition of extra reagent;

Measurement 2 is conducted;

Comparison of Measurement 1 value and Measurement 2 value. This step is necessary to determine if the amount of reagent is sufficient in relation to the measured hydrogen peroxide value. Measurement 2 is about half the reading of Measurement 1.

Empty measurement cell 15;

Rinse measurement cell 15 with sample water;

Fill and keep measurement cell 15 full until the next measurement is required.

The complete sequence in one embodiment takes about 2 minutes. The smallest wait time between two sequences is about 10 seconds. Multiple apparatuses may be added in the same location with offset measurement times to provide continuous accurate measurements of hydrogen peroxide concentrations in that area over time.

When developing the reagent for use with apparatus 100, consideration was taken for various degrees of water hardness and the presence of trace metals. The reagent can be used to measure the hydrogen peroxide content in water samples having a wide range of pH, temperature and water hardness.

The control unit 35 may also include a dosing and control algorithm that compares the measured $H_2O_2$ concentration to a set point that defines the desired concentration of $H_2O_2$ in the water treatment and distribution system from which the apparatus is diverting water to the apparatus 100 for measurement. The set point may be defined as a discrete value such as 8 ppm or as a range such as between 2-10 ppm. The control unit 35 is further configured to control a $H_2O_2$ dosing apparatus of the water treatment and distribution system in response to the measured $H_2O_2$ concentration and the set point. The dosing apparatus is located upstream of the apparatus 100 such that additions of $H_2O_2$ made by the dosing apparatus are monitored by the apparatus 100 and subsequent measurements are re-evaluated by the dosing algorithm relative to the set point. A water treatment and distribution system may have multiple apparatus 100 for measurement and multiple control units 35 distributed throughout the system. Alternatively, one control unit 35 may obtain input from multiple measurement apparatus 100 and control multiple dosing apparatus. An exemplary dosing and control algorithm is a Proportional-Integral-Derivative (PID) control algorithm. A PID control is a common control algorithm used in industry and has been universally accepted in industrial control. PID controllers have robust performance in a wide range of operating conditions and their functional simplicity allows for ease of operation.

Example 1

The objective of this example was to verify the accuracy of one embodiment of the present invention, in the lowest range of 1-5 ppm by testing samples having a known concentration of $H_2O_2$ in the range of 1-5 ppm.

The sample was prepared as follows: A 350 mg/L standard solution of hydrogen peroxide was prepared with 2 mL of 30% aqueous solution $H_2O_2$ (Perhydrol™), which was pipetted into a 2,000 ml volumetric flask. The solution was then topped with distilled water.

The exact concentration of this solution was determined analytically by multiple iodometric titrations (see Table 2, below). The average result of these titrations was taken to be the true concentration of the prepared solution of $H_2O_2$.

TABLE 2

| | Volume of sodium thiosulphate used in titration (mL) | Corresponding concentration of $H_2O_2$ (mg/L) |
|---|---|---|
| Titration 1 | 10.45 | 355 |
| Titration 2 | 10.10 | 344 |
| Titration 3 | 10.55 | 359 |

The final concentration of the $H_2O_2$ standard was calculated to be:

$$[H_2O_2] = \bar{X} = \frac{355 + 344 + 359}{3} = 353 \frac{mg}{l}$$

From the standard solution (350 mg/L $H_2O_2$) five dilutions were prepared with a final concentration of 5, 4, 3, 2 and 1 mg/L $H_2O_2$. The quantities were pipetted from the $H_2O_2$ standard solution into 100 mL volumetric flasks to achieve these concentrations are shown below in Table 3.

TABLE 3

| Target concentration (mg/L) | Volume pipetted from standard solution (ml) |
|---|---|
| 5 | 1.42 |
| 4 | 1.13 |
| 3 | 0.85 |
| 2 | 0.57 |
| 1 | 0.283 |

The apparatus of one embodiment of the present invention was then used to independently determine the concentrations in the above solutions of $H_2O_2$. Three measurement runs were taken for each sample. The results of the apparatus measurements and average values are presented in Table 4.

TABLE 4

| Predicted conc. $H_2O_2$ (mg/L) | Measured Values of Apparatus (mg/L) | | | Average of measured results (mg/L) with margin of error |
|---|---|---|---|---|
| | Run 1 | Run 2 | Run 3 | |
| 1.0 | 0.9 | 1.1 | 1.0 | 1.0 ± 0.1 |
| 2.0 | 2.0 | 2.1 | 2.0 | 2.0 ± 0.1 |
| 3.0 | 2.9 | 3.0 | 3.1 | 3.0 ± 0.1 |
| 4.0 | 4.0 | 3.9 | 4.0 | 4.0 ± 0.1 |
| 5.0 | 5.0 | 5.1 | 5.0 | 5.0 ± 0.1 |

The discrepancy between the predicted and measured values was assumed to be solely due to inaccuracies in the apparatus' ability to measure concentrations of $H_2O_2$. The values of the samples of $H_2O_2$ in solution measured by the apparatus in one embodiment of the present invention are linear. The apparatus itself is able to measure the concentration of $H_2O_2$ in solution with a degree of accuracy of 0.1 mg/L in the range of 1-5 mg/L $H_2O_2$.

Example 2

A standard curve was generated and digitized data on the X-axis (vertical) plotted relative to hydrogen peroxide concentration on the Y-axis (horizontal). Table 5 presents data for two known concentrations (Points A, B) of $H_2O_2$ and one unknown concentration (Point C).

TABLE 5

| Point | Measured value (X) | Concentration (Y) (ppm) |
|---|---|---|
| A | 208 | 21.4 |
| B | 92 | 42.23 |
| C | 142 | To be determined |

An equation to represent the line between two known points is determined. The known points are selected based on proximity to that of the unknown measurement such that the unknown lies between the two known points. In this case, for the selected known data points, the difference in X values (delta X) and the difference in Y values (delta Y) is calculated by:

Delta $X = Xa - Xb = 208 - 92 = 116$

Delta $Y = Ya - Yb = 21.4 - 42.23 = -20.83$

Slope $= dY/dX = -20.83/116 = -0.18$

Yc is the unknown $H_2O_2$ concentration represented by the coordinate Yc. Distance Xc:b from a known data point is calculated; $Xc - Xb = 142 - 92 = 50$ $Yc = (Xc - Xb)*slope + Yb = (142 - 92)*-0.18 + 42.23 = 33.23$ The unknown Yc can alternatively be calculated from point B $(Xc - Xa)$ $Yc = (Xc - Xa)*slope + Ya = (142 - 208)*-0.18 + 21.4 = 33.28$ While the invention has been described with respect to a specific apparatus and method for measuring hydrogen peroxide in water, and controlling the level of hydrogen peroxide in water, it may equally be applied to other apparatuses having various structures, so long as they include the elements as described herein.

The invention claimed is:

1. A method of measuring hydrogen peroxide levels in a water treatment system using a colorimetric assay, the method comprising:
   a. transferring a first water sample to a measuring cell;
   b. determining a first absorbance measurement of light at a selected wavelength as a null measurement;
   c. removing the first sample from the measurement cell;
   d. transferring an aliquot of a reagent compound to the measurement cell, the reagent compound capable of reacting with hydrogen peroxide to form a reaction product, the reaction product adapted to absorb light at the selected wavelength proportional to the amount of hydrogen peroxide in the water sample;
   e. filling the measurement cell with a second water sample containing hydrogen peroxide for reacting with the reagent compound;
   f. determining a second absorbance measurement of light at the selected wavelength as a test measurement;
   g. emptying the measurement cell and rinsing with sample water; and
   h. determining the difference between the first and second measurements and comparing the difference against a pre-determined standard curve of diluted hydrogen peroxide to determine and report the concentration of hydrogen peroxide in the water sample.

2. The method of claim 1, wherein the reagent compound is potassium bis(oxalato) oxotitanate (IV) DI.

3. The method of claim 2, wherein the selected wavelength is 470 nm.

4. The method of claim 1, wherein the reagent comprises potassium bis (oxalato) oxotitanate (IV) DI, EDTA disodium salt dihydrate and polyoxyethylene (23) lauryl ether mixed in a solvent.

5. The method of claim 4, wherein the solvent is sulfuric acid 99%: p.a. 10% solution.

6. The method of claim 1, wherein the predetermined standard curve comprises data points from 0 ppm to 150 ppm.

7. The method of claim 1, wherein the predetermined standard curve comprises data points from 0 ppm to 100 ppm.

8. The method of claim 1, wherein the concentration of hydrogen peroxide in the water sample is determined to an accuracy of 0.1 mg/L.

9. The method of claim 1, wherein the water treatment system comprises drinking water.

\* \* \* \* \*